United States Patent
Siuda (10) Patent No.: US 12,296,135 B2
(45) Date of Patent: May 13, 2025

(54) PENETRABLE CLOSED SHEATH TIP

(71) Applicant: GYRUS ACMI, INC, Westborough, MA (US)

(72) Inventor: Anthony H. Siuda, Redmond, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 802 days.

(21) Appl. No.: 16/205,655

(22) Filed: Nov. 30, 2018

(65) Prior Publication Data
US 2020/0171292 A1 Jun. 4, 2020

(51) Int. Cl.
| | |
|---|---|
| A61M 39/04 | (2006.01) |
| A61B 1/018 | (2006.01) |
| A61B 10/00 | (2006.01) |
| A61B 18/14 | (2006.01) |
| A61M 39/02 | (2006.01) |

(52) U.S. Cl.
CPC .......... *A61M 39/045* (2013.01); *A61B 1/018* (2013.01); *A61B 10/0045* (2013.01); *A61B 18/1482* (2013.01); *A61M 2039/0279* (2013.01); *A61M 2205/502* (2013.01); *A61M 2207/00* (2013.01)

(58) Field of Classification Search
CPC ........ A61M 39/045; A61M 2039/0279; A61M 2205/502; A61M 2207/00; A61B 1/018; A61B 10/0045; A61B 18/1482
USPC .......................................................... 606/1
See application file for complete search history.

(56) References Cited

U.S. PATENT DOCUMENTS

| | | | |
|---|---|---|---|
| 4,531,943 A | 7/1985 | Tassel et al. | |
| 6,306,124 B1 * | 10/2001 | Jones | A61M 25/0012 604/167.04 |
| 6,497,845 B1 * | 12/2002 | Sacherer | G01N 33/48778 422/561 |
| 6,730,081 B1 * | 5/2004 | Desai | A61B 17/00234 606/40 |
| 9,901,296 B2 * | 2/2018 | Fritz | A61B 5/15142 |
| 2008/0228171 A1 * | 9/2008 | Kugler | A61B 17/3478 604/529 |
| 2010/0261972 A1 * | 10/2010 | Widenhouse | A61B 17/3462 600/206 |
| 2015/0105729 A1 | 4/2015 | Valeti et al. | |
| 2017/0079519 A1 | 3/2017 | Sung et al. | |

* cited by examiner

*Primary Examiner* — Aaron F Roane
(74) *Attorney, Agent, or Firm* — Schwegman Lundberg & Woessner, P.A.

(57) ABSTRACT

Disclosed embodiments include apparatuses, systems, and methods for providing a sheath tip with a solid end surface configured to be pierceable by an instrument, where the solid end surface is configured to distribute force of impact with a tissue surface across the solid end surface. In an illustrative embodiment, an apparatus includes a closed sheath tip has a solid end surface configured to be pierceable by an instrument. The closed sheath tip is configured to be disposed at a distal end of a sheath defining therein a lumen configured to convey the instrument therethrough. When the closed sheath tip is presented at a tissue surface, the solid end surface of the closed sheath tip is configured to distribute force of impact with the tissue surface across the solid end surface and to permit the instrument to pierce the solid end surface and extend therethrough toward the tissue surface.

20 Claims, 6 Drawing Sheets

PENETRABLE CLOSED SHEATH TIP

FIELD

The present disclosure relates to a sheath for extending an elongated instrument therethrough.

BACKGROUND

The statements in this section merely provide background information related to the present disclosure and may not constitute prior art.

The ability to access tissue within a patient's body without invasive surgery allows for ever-improving types of analysis, diagnosis, and treatment with reduced pain, reduced recovery time, and a reduced risk of complications. By way of two examples, endoscopic and catherization techniques have enabled evaluation and treatment of numerous internal lesions without invasive surgery.

For example, suspected or actual lesions may be sampled or treated by extending an elongated medical instrument, such as a sampling needle, through a sheath that is positioned by an insertion control system, such as a bronchoscope or an endoscope. The sheath may be extended from the insertion control system to position the elongated medical instrument, then the elongated instrument itself may be deployed for sampling or treatment.

Use of the insertion control system, while possibly avoiding invasive surgery, may pose its own challenges. For example, because the insertion control system may operate in tight spaces, sampling or treating target tissue at a desired position within in a body while minimizing or attempting to avoid or minimize trauma to the tissue at or near the desired position or other undesirable effects resulting from contact between the insertion control system and tissue walls may pose a challenge.

SUMMARY

Disclosed embodiments include apparatuses, systems, and methods for providing a sheath tip with a solid end surface configured to be pierceable by an instrument, where the solid end surface is configured to distribute force of impact with a tissue surface across the solid end surface. It will be appreciated that various disclosed embodiments seek to help reduce or avoid tissue damage upon a sheath being extended to convey an elongated instrument for sampling or treatment or other undesirable effects resulting from the sheath pushing against tissue surfaces.

In an illustrative embodiment, an apparatus includes a closed sheath tip has a solid end surface configured to be pierceable by an instrument. The closed sheath tip is configured to be disposed at a distal end of a sheath defining therein a lumen configured to convey the instrument therethrough. When the closed sheath tip is presented at a tissue surface, the solid end surface of the closed sheath tip is configured to distribute force of impact with the tissue surface across the solid end surface and to permit the instrument to pierce the solid end surface and extend therethrough toward the tissue surface.

In another illustrative embodiment, a system includes a sheath defining therein a lumen and configured to be extendable toward a tissue surface, an elongated medical instrument configured to be delivered through the lumen in the sheath, an insertion control system configured to convey the sheath to a desired location within a body, and an instrument control system configured to direct operation of the elongated medial instrument when the elongated medical instrument reaches a desired position. The system also includes a closed sheath tip positioned at a distal end of the sheath, the closed sheath tip having a solid end surface configured to be pierceable by the elongated medical instrument. The system is configured such that, when the closed sheath tip is presented at the tissue surface, the solid end surface of the closed sheath tip is configured to distribute force of impact with the tissue surface across the solid end surface and to permit the instrument to pierce the solid end surface and extend therethrough toward the tissue surface.

In a further illustrative embodiment, a method includes preparing an elongated instrument for being conveyed into a body through a lumen in a sheath. The sheath is to be extended toward a tissue. The sheath includes a closed sheath tip at a distal end of the sheath so that, when the closed sheath tip is presented at a tissue surface, the solid end surface of the closed sheath tip is configured to distribute force of impact with the tissue surface across the solid end surface while permitting the instrument to pierce the solid end surface and extend therethrough toward the tissue surface. The sheath that conveys the elongated instrument into the body is inserted into the body. The instrument is extended through the lumen to pierce the solid end surface of the closed sheath tip toward the tissue surface.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings.

DETAILED DESCRIPTION

The following description is merely illustrative in nature and is not intended to limit the present disclosure, application, or uses. It will be noted that the first digit of the three-digit reference numbers corresponds to the number of the figure in which the element first appears.

The following description explains, by way of illustration only and not of limitation, various embodiments of closed sheath tips to help reduce or seek to prevent undesirable effects resulting from extension of a sheath toward a surface, as well as systems including such closed sheath tips and methods of using the same. As will be described in detail below, in various illustrative embodiments the closed sheath tips include closed sheath tips configured to present a solid end surface such that, upon impacting a tissue wall, force of the impact is distributed across the solid end surface to minimize or reduce trauma to the tissue surface that might be caused by impact across multiple edges of an open-ended sheath. The solid end surface of the closed sheath tip is permeable by an instrument inserted therethrough, thereby minimizing or reducing trauma to the tissue surface while not interfering with the object for deploying the sheath at the tissue surface.

Figure 1:
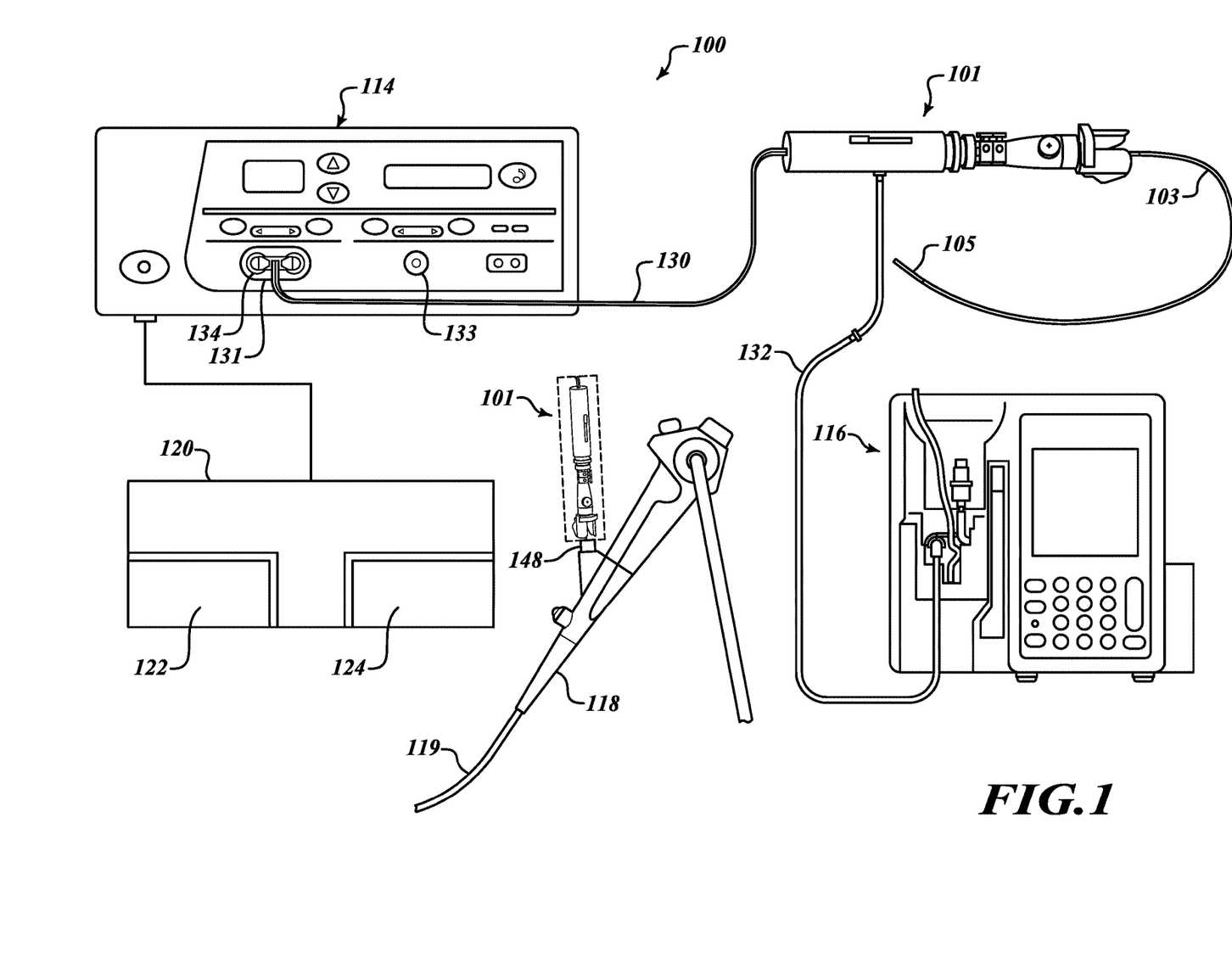
FIG. 1 is a block diagram in partial schematic form of an illustrative system for sampling or treating tissue.

Referring to FIG. 1, in various embodiments an illustrative system 100 is provided for sampling or treating tissue at a reference point in an anatomical region of a patient (not shown in FIG. 1). For one example, the system 100 may include a sampling device with a vacuum system for drawing a sample via a sampling needle. In some embodiments, the system 100 may be a bipolar radio frequency (RF) system, as desired, for using electrical current to ablate or coagulate tissue in a patient. In some other embodiments, the system 100 may include a mechanical or laser-based cutting system for incising tissue in a patient. Any such system may involve insertion of an elongated instrument into a patient to perform a desired procedure, and any such elongated instrument may be inserted into a patient via a sheath which may desirably end in a sheath tip as disclosed herein.

In some embodiments, the system 100 includes an elongated medical instrument controllable by a user interface 101, one or more instrument control systems 114 and 116, an insertion control system 118, and various supporting apparatuses. The user interface 101 may include a positioning device for positioning a distal end 105 of a sheath 103, equipped with a closed sheath tip 107, relative to a position of interest in a body (not shown in FIG. 1). The user interface 101 also may be configured to direct a position of an elongated instrument (not shown in FIG. 1) that is housed within the sheath 103. The elongated instrument, for example, may include, for example, a sampling needle, as described below with reference to FIGS. 5A-5C, one or more electrodes, an imaging device, a probe, a cutting device, or any other elongated device. The one or more control systems 114 and 116 may be coupled to the elongated instrument and include devices to draw fluid or tissue, provide electrical current, provide fluid, monitor sensor data, or to perform other functions.

The insertion control system 118 may include a bronchoscope, an endoscope, or another insertion system configured to maneuver an insertion device 119 that may be equipped with a steering mechanism as well as optical, ultrasound, or other sensors to monitor the course of the insertion device 119. The user interface 101 may be received into the insertion control system 118 so that the insertion control system 118 at a port 148 for the insertion control system 118 so that the insertion control system 118 may direct the insertion device 119 to convey the distal end 105 of the sheath 103 to a desired location in a body (not shown in FIG. 1) where the user interface 101 then may be used to manipulate an associated elongated instrument to perform a desired function.

The system may represent any number of sampling or treatment systems. For one example, the system 100 may be a sampling system to collect a tissue sample using a sampling needle, such as described further below with reference to FIGS. 4 and 5A-5C. In such case, the insertion control system 118 may include a bronchoscope if the sample is to be collected from a respiratory system or an endoscope if the sample is to be collected from a digestive system. One instrument control system 114 may be used to receive and process sensor data and be operated by controls 120, 122, and 124. Another instrument control system 116 may be a pump or other vacuum source to draw a tissue or fluid sample from the sampling needle that may extend from the distal end 105 of the sheath 103 through the closed sheath tip 107.

For another example, the system 100 may be a cutting system for cutting through a tissue obstruction. In such case, the insertion control system 118 may include an endoscope to direct the if the sample is to be collected from a digestive system. One instrument control system 114 may be used to receive and process sensor data and be operated by controls 120, 122, and 124. Another instrument control system 116 may be a cutting control system to motivate a reciprocating and/or rotating cutting apparatus extending from the distal end 105 of the sheath 103.

For still another example, the system 100 may be an electrosurgical radio frequency (RF) system for ablating, cauterizing, or coagulating tissue. In such case, the insertion control system 118 may include a bronchoscope if the sample is to be collected from a respiratory system or an endoscope if the sample is to be collected from a digestive system. One instrument control system 114 may be a generator operating as a switchable power source 114 to apply electrical power to an elongated instrument extending from the distal end 105 of the sheath. The user interface 101 electrically communicates with the switchable power source 114 though an electrical conductor 130. In some embodiments, the electrical conductor 130 is connected to an outlet 131 when the system is operated in a bipolar mode. The electrical conductor 130 may be coupled with the outlet 131 using an electrical connector 134 configured to electrically engage the outlet 131. The switchable power source 114 can be operated with the use of a foot operated unit 120 electrically connected to the switchable power source 114. The foot operated unit 120 may include, for example, a pedal 122 that instructs the switchable power source 114 to apply electrical power to electrode(s) (described below) to cut and/or ablate tissue and a pedal 124 that instructs the generator 114 to apply a lower quantity of electrical power to the electrode(s) to coagulate tissue.

The user interface 101 is further connected to the conductive fluid source 116 with a tube 132 that facilitates the flow of liquid, for example saline solution or another conductive fluid, from the conductive fluid source 116 to the user interface 101. Another instrument control system 116 may be a conductive fluid source 116, such as an infusion pump controllable by a switch, to provide a conductive fluid to the distal end 105 of the sheath 103, where the conductive fluid may be vaporized by applied electrical power to generate heat to ablate or cauterize tissue.

The system 100 may include any number of medical systems or non-medical systems in which an elongated instrument is extended via a sheath 103 to perform an operation, and closed sheath tips in accordance with the present disclosure may be applied to the distal end 105 of the sheath 103 to facilitate such operations. Embodiments of the closed sheath tips of the present disclosure are not limited to use with any particular systems or functions. Any applications for use of the closed sheath tips of the present disclosure are provided solely for illustration and should not be taken as limiting.

Figure 2:
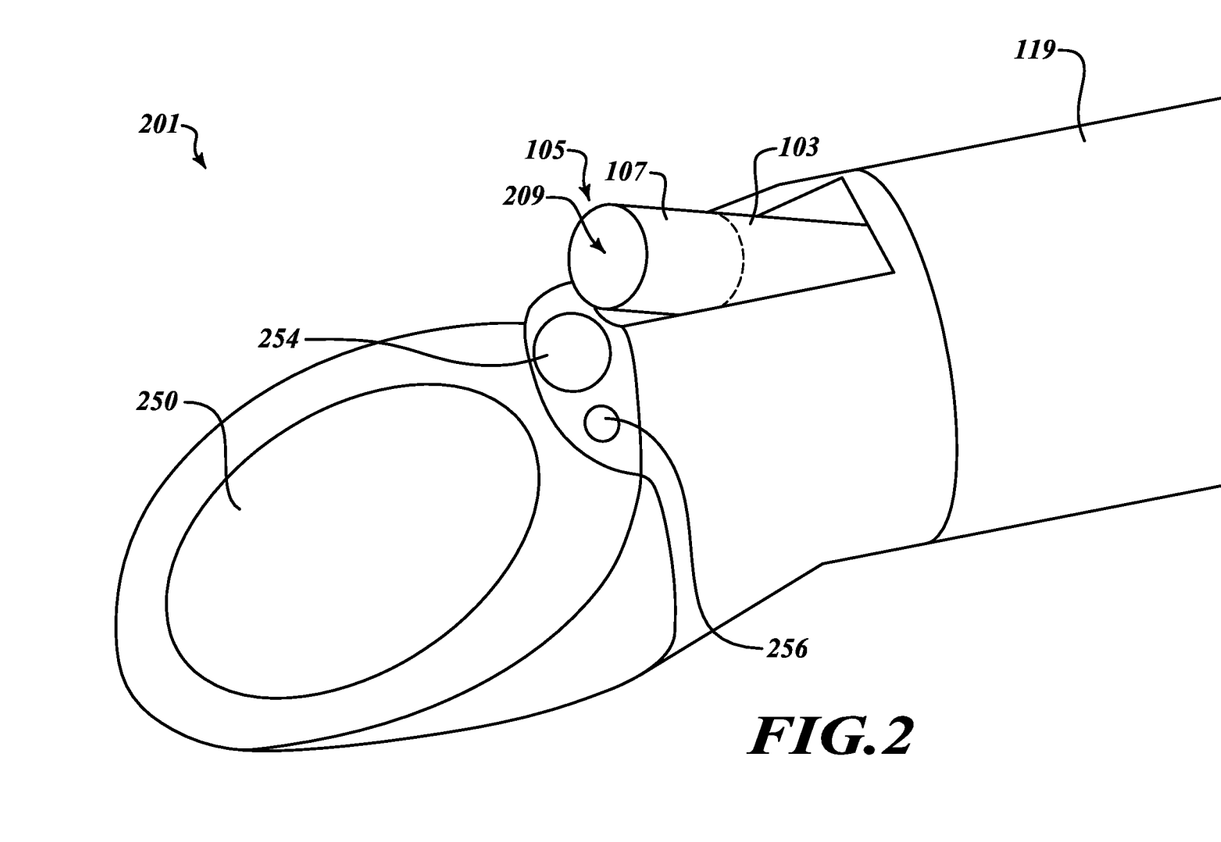
FIG. 2 is a perspective view of a head on an insertion device including a sheath fitted with an illustrative closed sheath tip.

Referring to FIG. 2, a head 201 of the insertion device 119 includes various sensor devices or related devices 250, 254, and 256 usable in positioning the distal end 105 of the sheath 103 (FIG. 1). For example, the head 201 may support an ultrasound transducer 250 that emits ultrasound energy and receives reflected ultrasound energy. The head 201 also may support a camera 254, for which a light source 256 may be provided to illuminate a region adjacent the head 201. The ultrasound transducer 250 and/or the camera 254 may be used to identify lesions or other regions of interest to be sampled or treated by an elongated instrument (not shown in FIG. 2) to be conveyed through the sheath 103.

The distal end 105 of the sheath 103 defines therein a lumen (not shown in FIG. 2) through and from which the elongated instrument (also not shown in FIG. 2) may extend. The distal end 105 of the sheath 103 may incorporate or be fitted with an embodiment of a closed sheath tip 107 as further described with reference to FIGS. 6A-6D. The closed sheath tip 107 has a solid end surface 209. The solid end surface 209 is intended to distribute force of an impact between the distal end 105 of the sheath 103 and a tissue surface (not shown in FIG. 2).

In an illustrative embodiment, the solid end surface 209 of the closed sheath tip 107 covers an end of the lumen at the distal end 105 of the sheath 103. The closed sheath tip 107 thereby reduces a number of edges, such as the inner edges of the sheath 103 around the lumen that may potentially be presented against a tissue surface (not shown in FIG. 2) when the distal end 105 of the sheath 103 impacts a tissue surface, as is further explained with reference to FIG. 4. Once the distal end 105 of the lumen 103 has been directed to a desired location, such as by the insertion device 119, the elongated instrument may be extended through the solid end surface 209 of the closed sheath tip 107. The elongated instrument pierces the solid end surface 209 of the closed sheath tip 107, enabling the elongated instrument to perform one or more desired actions.

Figure 3:
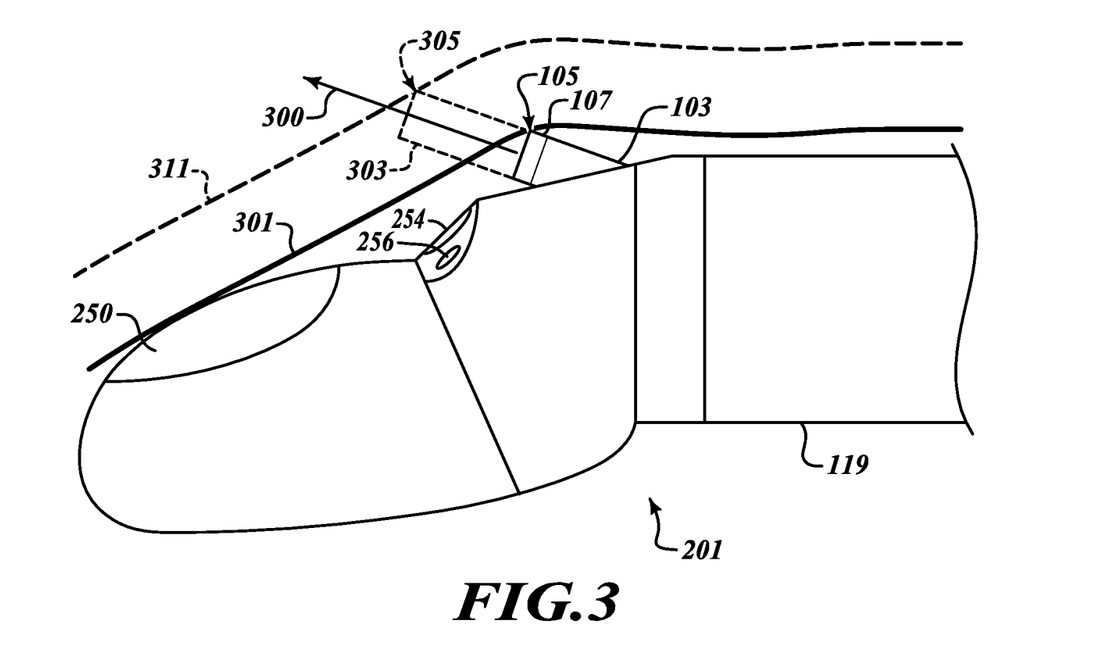
FIG. 3 is a side view of the head of the insertion device of FIG. 2 illustrating extension of the sheath having an illustrative closed sheath tip.

Referring to FIG. 3, the head 201 is disposed adjacent a tissue surface 301, such as an interior surface of a bodily tract into which the head 201 may be inserted. The head 201 is in position for extension of the sheath 103. When deployed, the sheath 103 extends along an axis 300 as shown by the dotted line representing the sheath 103 after it has been moved into an extended position 303. With the sheath in the extended position 303, an extended distal end 305 of the sheath 103 may impact the tissue surface 301 with enough force to potentially cause trauma to and/or to distend or displace the tissue surface, as shown by the dashed line representing an impacted tissue surface 311. The closed sheath tip 107 (and its solid end surface (not shown in FIG. 3)) helps to distribute the force of the impact of the extended distal end 305 of the sheath 103 and the impacted tissue surface 311, as described below with reference to FIG. 4.

Figure 4:
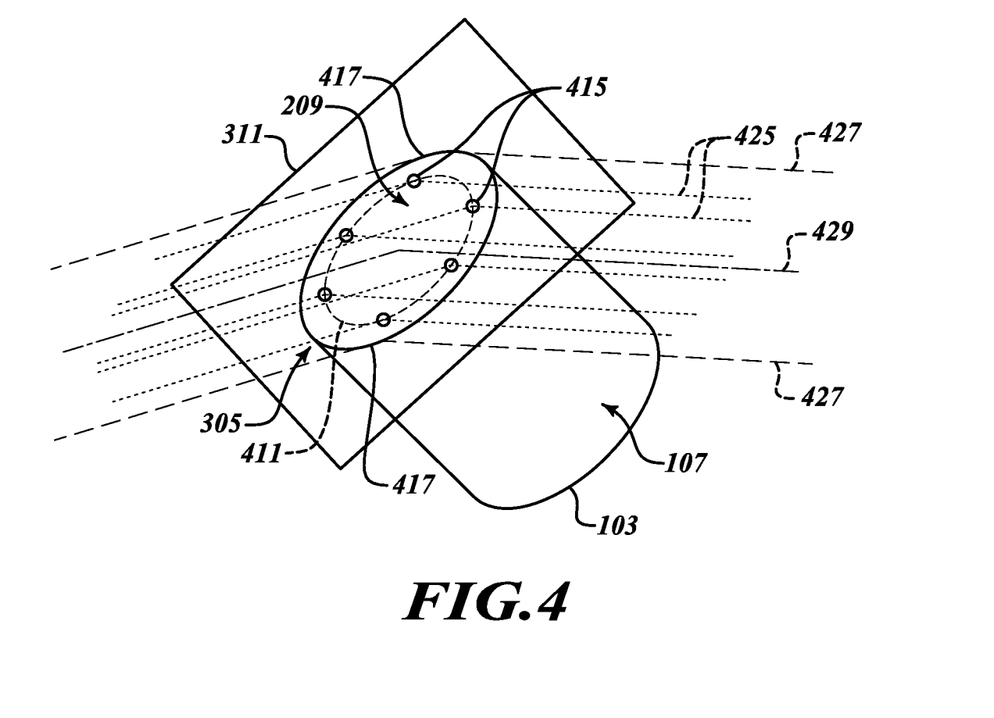
FIG. 4 is a perspective view in partial schematic form of the closed sheath tip in contact with a tissue surface showing distribution of impact force.

Referring to FIG. 4, the solid end surface 209 of the closed sheath tip 107 distributes impact force between the distal end 105 of the sheath 103 and the impacted tissue surface 311. When the extended distal end 305 of the sheath 103 contacts the impacted tissue surface 311, potential contact points 417 along outer edges of the extended distal end 305 of the sheath 103 may cause strain along the impacted tissue surface 311 as represented by dashed lines 427. In addition, in a sheath 103 without a closed end sheath tip 107, an open end 411 (as represented by the dotted-line opening) may present localized contact points 415 between the open end 411 and the impacted tissue surface 311, thereby potentially resulting in strain or trauma along the impacted tissue surface 311 as represented by dotted lines 425. By contrast, a closed sheath tip 107 that presents a solid end surface 209 to the impacted tissue wall 311 can help present fewer edges and, thus, can help reduce the number of localized contact points 413 between the extended distal end 305 of the sheath 103 and the impacted tissue surface 311. Instead of potential localized contact points 415 being presented around an open end 411, resulting strain instead is distributed across the solid end surface 209 of the closed sheath tip 107. This resultant strain distribution is represented by dotted and dashed line 429. By distributing the strain across the solid end surface 209, a degree of localized strain that may have occurred at localized contact points 415 is reduced, thereby potentially helping to reduce a degree of trauma that may be inflicted on the impacted tissue surface 311.

Figure 5A:
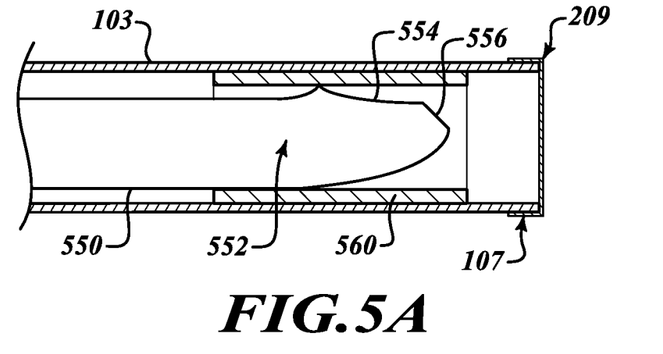
FIGS. 5A, 5B, and 5C are cutaway views of an end of a sheath configured with a closed sheath tip showing deployment of an instrument through the solid end of the closed sheath tip.
Figure 5B:
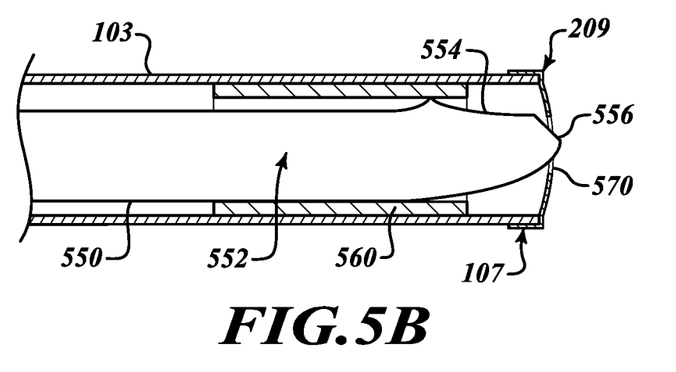
Figure 5C:
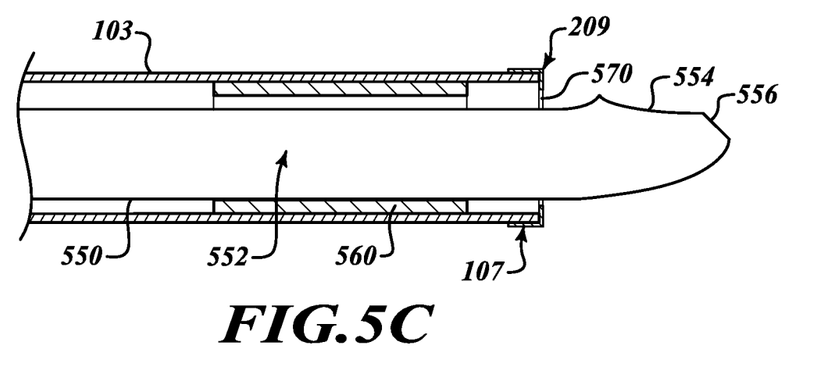

Referring to FIGS. 5A-5C, deployment of an instrument via a lumen in the sheath 103 and through the closed sheath tip 107 is shown. Referring to FIG. 5A, the instrument may include an elongated medical instrument 550, such as a sampling needle configured to draw a tissue sample from a tissue surface, lesion, or other body. An elongated medical instrument 550 in the nature of a sampling needle may include an interior lumen 552 that terminates in an open sampling end 554. The elongated medical instrument 550 may terminate in a pointed or sharpened end or edge 556. To protect the sheath 103, a rigid insert 560 may be disposed within the sheath 103 to prevent the sharpened end or edge 556 from piercing the sheath 103. The elongated instrument 550 may be extended from the sheath 103 to collect a sample of tissue (not shown) that is then drawn through the lumen 552 by a pump or vacuum source for collection and testing and included as an instrument control system 116 in the system 100 as described with reference to FIG. 1.

Referring to FIG. 5B, the elongated medical instrument 550 is extended to pierce the solid end surface 209 of the closed sheath tip 107. The elongated medical instrument 550 may be extended or otherwise directed to extend by the user interface 101 (FIG. 1) of the system 100. The user interface 101 may include a lever or other control surface mechanically coupled with the elongated medical instrument 550 to enable an operator to cause the elongated medical instrument to be extended. When the elongated medical instrument 550 is extended, the pointed or sharpened end or edge 556 of the elongated medical instrument 550 pierces the solid end surface 209 of the closed sheath tip 107, thereby forming an opening 570 in the closed end surface 209. The solid end surface 209, thus, is a membrane configured to be pierceable by the elongated medical instrument 550. As the pointed or sharpened end or edge 556 of the elongated medical instrument 550 passes through the solid end surface 209, the pointed or sharpened end or edge 556 may then penetrate a tissue surface (not shown in FIG. 5B). In the configuration shown in FIG. 5B, the open sampling end 554 is not yet extended through the solid end surface 209 of the closed sheath tip 107 and, thus, is not fully deployed.

Referring to FIG. 5C, the elongated medical instrument 550 is extended to an operational position. Using the user interface 101 (FIG. 1), the elongated medical instrument 550 is further extended through the solid end surface 209 of the closed sheath tip 107 to position the elongated medical instrument 550 for operation. In the example of FIG. 5C, the elongated medical instrument 550, which is in the nature of a sampling needle, is extended through use of the user interface 101 (FIG. 1) or another device or means to extend the open sampling end 554 into the tissue surface (not shown) to collect a sample. The elongated medical instrument 550 is further extended through the opening 570 previously started and/or formed by the pointed or sharpened end or edge 556 of the elongated medical instrument 550 in the solid end surface 209 of the closed sheath tip 107, as shown in FIG. 5B.

Once the elongated medical instrument 550 is extended to place the open sampling end 554 or other operational element of the elongated medical instrument 550 to a desired position, the elongated medical instrument may be activated. For example, when the elongated medical instrument 550 is a sampling needle, a vacuum source may be used to draw a sample into and through the lumen 552 of the elongated medical instrument to retrieve a sample from the tissue surface (not shown in FIG. 5C). However, it will be appreciated that the elongated medical instrument 550 may include any one or more of a number of instruments including electrodes, cutting devices, other apparatuses, and the like. As such, it will be appreciated that the sampling needle shown and described herein is used only by way of illustration and not of limitation. In addition, it will be appreciated that other types of elongated instruments other than medical instruments may be used as desired with a closed sheath tip.

Figure 6A:
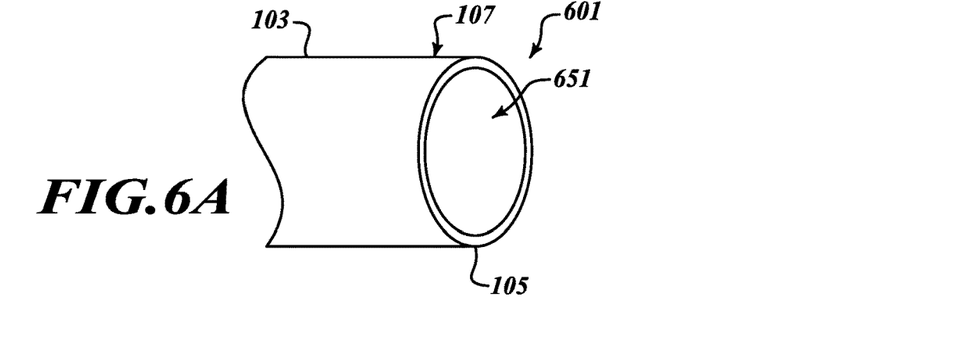
FIGS. 6A, 6B, 6C, and 6D are perspective views of other illustrative forms of a closed sheath tip attachable to a distal end of a sheath.

Referring to FIGS. 6A-6D, the closed sheath tip may be formed or attached to the sheath in a number of different ways. Referring to FIG. 6A, in a first exemplary embodiment 601, a closed sheath tip 107 may be integrally formed as part of the sheath 103. In such a configuration, a solid end surface 651 is molded or otherwise formed at the distal end 105 of the sheath 103 when the sheath 103 is created. In an illustrative embodiment, the solid end surface 651 is formed, such as by injection-molding or as a step in an extrusion process, onto the distal end 105 of the sheath 103 to form the closed sheath tip 207.

Figure 6B:
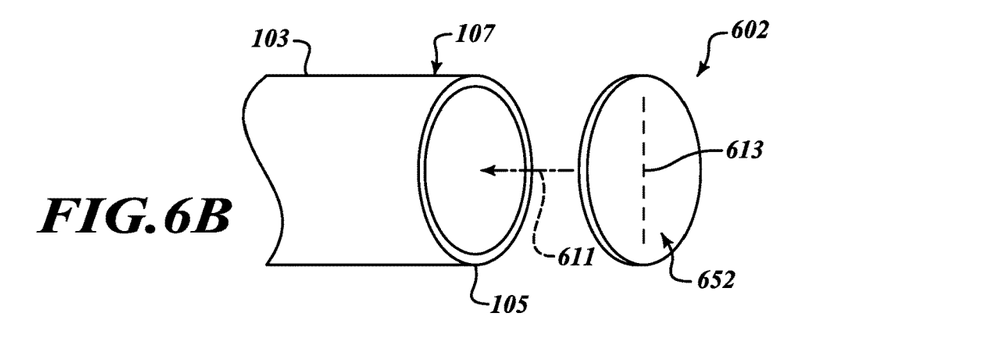

Referring to FIG. 6B, in another illustrative embodiment 602, the closed sheath tip 107 is formed by attaching a solid end surface 652 to the distal end 105 of the sheath 103 by a process such as, for example, adhesive attachment or heat welding. In such illustrative embodiments, the solid end surface 652 may have outer dimensions approximately matching those of the distal end 105 of the sheath 103 so that the solid end surface generally covers the distal end 105 of the sheath 103 once it is attached thereto. The solid end surface 652 may be composed of a same substance as the sheath 103 or a different material that, for example, may be softer, more pliable, or more susceptible to being pierced by the pointed or sharpened end or edge 556 of the elongated medical instrument 550, as described with reference to FIGS. 5B and 5C. The solid end surface 209, in the exemplary embodiment of a closed sheath tip 107 of FIG. 6B or in other embodiments of closed sheath tip 107 may also be scored, perforated, or partially perforated at a point or along a line at a location 613 of the solid end surface 652 to facilitate penetration by the pointed or sharpened end or edge 556 of the elongated medical instrument 550, or by a non-sharpened end or another elongated instrument.

In the illustrative embodiment shown in FIG. 6B, the closed sheath tip 107 is formed by moving the solid end surface 652 in a direction 611 onto the distal end 105 of the sheath 103. The solid end surface 652, which forms the closed sheath tip 107 in connection with the distal end 105 of the sheath 103, is configured to be attached to the distal end 105 of the sheath 103 by adhesive or by heat welding. The closed sheath tip 107 is formed by securing the solid end surface 652 to the distal end 105 of the sheath 103 with adhesive, heat welding, or another suitable attachment process or mechanism.

Figure 6C:
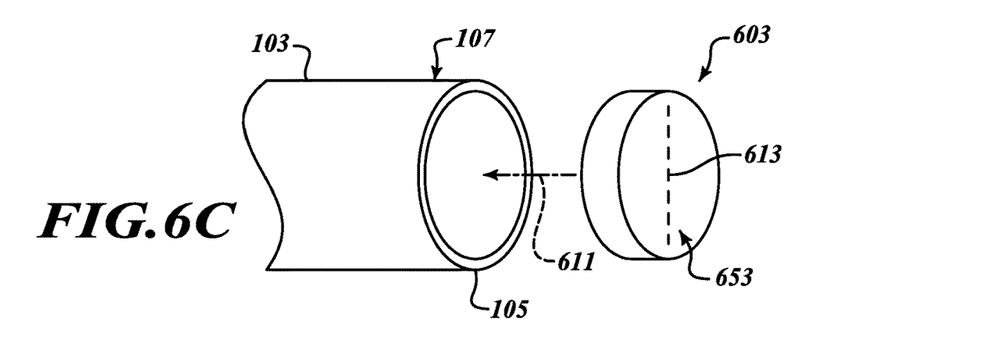

Referring to FIG. 6C, in another illustrative embodiment 603, the closed sheath tip 107 suitably inserts a solid end surface 653 into the distal end 105 of the sheath 103 and attaches the solid end surface 653 to the distal end 103 of the sheath 105 by a process such as, for example, adhesive attachment or heat welding. The solid end surface 653 may have outer dimensions that may allow the solid end surface 653 to be received within the distal end 105 of the sheath 103 and that may allow tolerance for adhesive or another attachment mechanism. The solid end surface 653 may be composed of a same substance as the sheath 103 or a different material that, for example, may be softer, more pliable, or more susceptible to being pierced by the pointed or sharpened end or edge 556 of the elongated medical instrument 550, as described with reference to FIGS. 5B and 5C. The solid end surface 653, such as that described for the illustrative sheath tip 107 (FIG. 6B), may also be scored, perforated, or partially perforated at a point or along a line at a location 613 of the solid end surface 653 to facilitate penetration by the pointed or sharpened end or edge 556 of the elongated medical instrument 550, or by a non-sharpened end or another elongated instrument. In the illustrative embodiment of FIG. 6B, the closed sheath tip 107 is formed by moving the solid end surface 653 in a direction 611 into the distal end 105 of the sheath 103. The solid end surface 653 is then secured to the distal end 105 of the sheath 103 with an adhesive, by heat welding, or another suitable attachment process or mechanism.

Figure 6D:
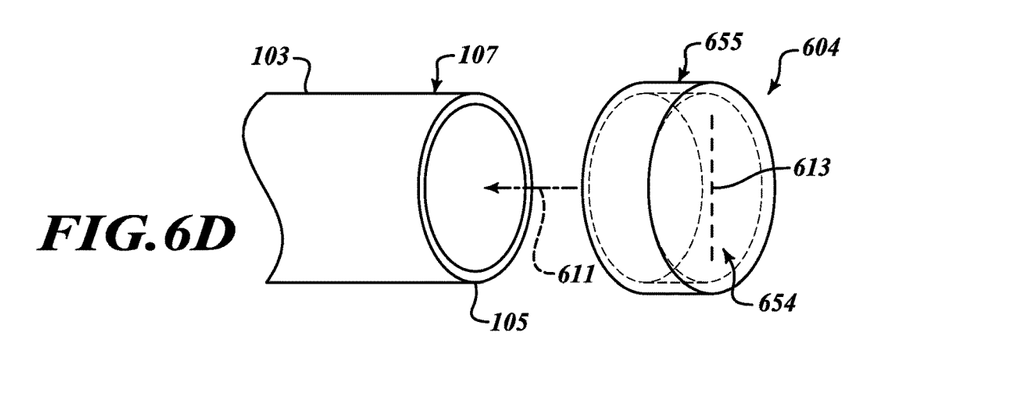

Referring to FIG. 6D, in another illustrative embodiment 604, the closed sheath tip 107 may include a solid end surface 654 and a coupling 655 joined or molded with the solid end surface 654 to facilitate attachment of the closed sheath tip 107 to the distal end of the sheath 103 and to attach the closed sheath tip 107 to the distal end 103 of the sheath 105 by a process such as, for example, adhesive attachment or heat welding. The coupling 655 may have outer dimensions as desired that may allow the coupling 655 to be joined to either the inner or outer surfaces of the distal end 105 of the sheath 103 and may allow tolerance for adhesive or another attachment mechanism. The solid end surface 654 and/or the coupling 655 may be composed of same or different materials, including the same substance as the sheath 103 or a different material that, for example, may be softer, more pliable, or make the solid end surface 654 more susceptible to being pierced by the pointed or sharpened end or edge 556 of the elongated medical instrument 550, as described with reference to FIGS. 5B and 5C. The solid end surface 654, in the illustrative embodiment of a closed sheath tip 107 shown in FIG. 6B or in other embodiments of closed sheath tip 107 may also be scored, perforated, or partially perforated at a point or along a line at a location 613 of the solid end surface 654 to facilitate penetration by the pointed or sharpened end or edge 556 of the elongated medical instrument 550, or by a non-sharpened end or another elongated instrument. In the illustrative embodiment shown in FIG. 6D, the closed sheath tip 107 suitably is attached by moving the closed sheath tip 107 in a direction 611 to move the coupling 655 into or onto the distal end 105 of the sheath 103. The closed sheath tip 107 is then secured to the distal end 105 of the sheath 103 by attaching the solid end surface 654 and/or the coupling 655 to the distal end 105 of the sheath 103 with an adhesive, by heat welding, or another suitable attachment process or mechanism.

Figure 7:
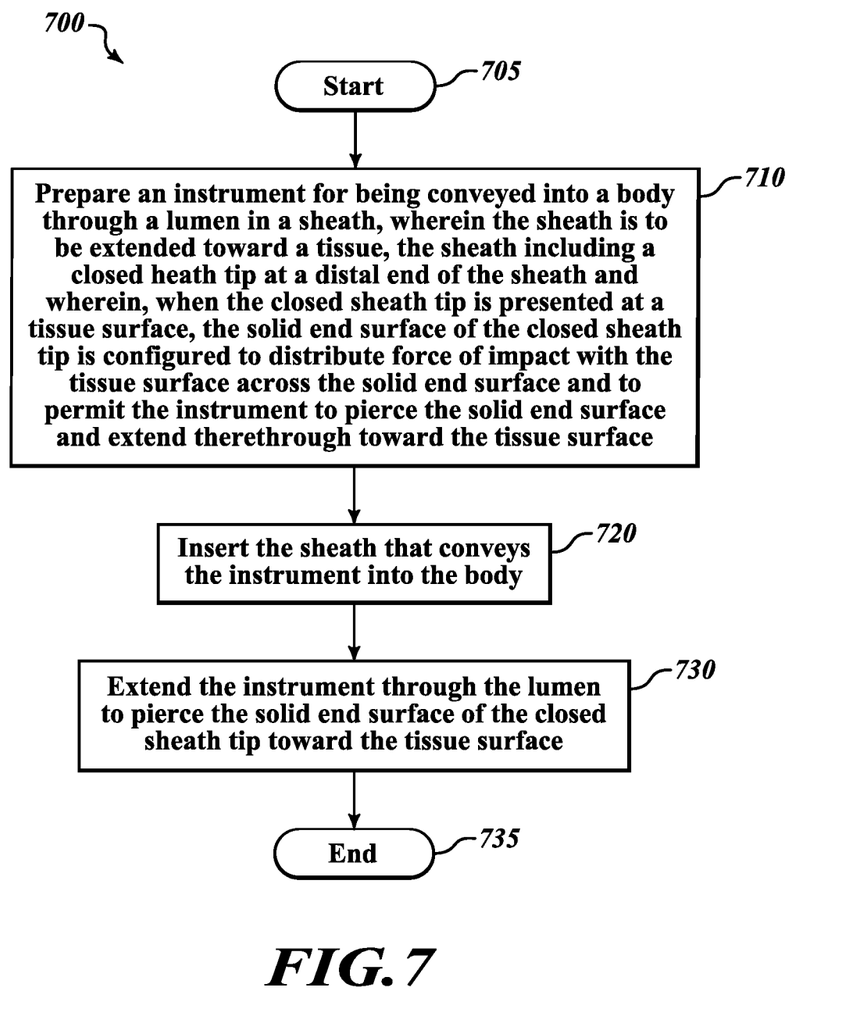
FIG. 7 is a flow diagram of an illustrative method of operating an apparatus equipped with a closed sheath tip.

Referring to FIG. 7 an illustrative method 700 of using a closed sheath tip in deploying an elongated instrument via a sheath is provided. The method 700 starts at a block 705. At a block 710, an instrument is prepared for being conveyed into a body through a lumen in a sheath, wherein the sheath is to be extended toward a tissue. The sheath includes a closed heath tip at a distal end of the sheath. When the closed sheath tip is presented at a tissue surface, the solid end surface of the closed sheath tip is configured to distribute force of impact with the tissue surface across the solid end surface and to permit the instrument to pierce the solid end surface and extend therethrough toward the tissue surface. Preparation for using the elongated instrument may include, for example, inserting a sheath housing an elongated instrument into an insertion system, maneuvering the insertion system to a desired location in a body, or other steps that logically may proceed deploying or using the elongated instrument. The configuration of the closed sheath tips useable in accordance with the illustrative method 700 are described with reference to FIGS. 2, 3, 4, 5A-5C, and 6A-6D.

At a block 720, the sheath that conveys the instrument is inserted into the body. The insertion of the instrument is described with reference to FIGS. 1, 2, 3, 4, and 5A-5C.

At a block 730, the instrument is extended through the lumen to pierce the solid end surface of the closed sheath tip toward the tissue surface, where the instrument may be operated as intended or desired. The method 700 ends at a block 735.

It will be appreciated that the present descriptions of the sheath tips being used in the insertion of elongated instruments into a body via a sheath are not limiting to either the types of elongated instruments described or to use with medical instruments in a biological body. Sheath tips in the nature of those described could be used in any application where a lumen may contact a surface to which damage could result from impact of the lumen against the surface.

It will also be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus comprising:
    a sheath including a flexible elongated body extending from a proximal end to a distal end and configured to deliver an elongated medical instrument to a target location within a patient;
    an insertion device configured to position a distal end of the sheath adjacent the target location, the insertion device including a lumen terminating at a head, the lumen configured to deliver the sheath to the target location along an extension axis, wherein the head includes an ultrasound transducer; and
    a closed sheath tip disposed on a distal end of the sheath, the closed sheath tip having a solid end surface, wherein the solid end surface is configured to be pierceable by the elongated medical instrument having at least one of a pointed end and a sharpened edge, and wherein the sheath defines therein a second lumen configured to convey the elongated medical instrument therethrough such that, when the closed sheath tip is presented at a tissue surface, the solid end surface of the closed sheath tip is configured to distribute force of impact with the tissue surface across the solid end surface and to permit the at least one of the pointed end and the sharpened edge the medical instrument to pierce the solid end surface and extend therethrough toward the tissue surface.

2. The apparatus of claim 1, wherein the closed sheath tip is formed integrally as part of the sheath at the distal end of the sheath.

3. The apparatus of claim 1, wherein the closed sheath tip is formed by one of attaching the solid end surface to the distal end of the sheath and attaching the solid end surface within the distal end of the sheath.

4. The apparatus of claim 3, wherein the closed sheath tip includes a coupling configured to facilitate attachment with the sheath by engaging at least one side of the sheath adjacent the distal end of the sheath.

5. The apparatus of claim 3, wherein the closed sheath tip is configured to be adhesively attached to the distal end of the sheath.

6. The apparatus of claim 3, wherein the closed sheath tip is configured to be heat-welded to the distal end of the sheath.

7. The apparatus of claim 1, wherein the solid end surface includes a membrane configured to be pierceable by the at least one of the pointed end and the sharpened edge of the medical instrument.

8. The apparatus of claim 1, wherein the solid end surface includes a flexible section configured to be pierceable by the at least one of the pointed end and the sharpened edge of the medical instrument and to at least one of compress and deform upon impact with the tissue surface.

9. The apparatus of claim 1, wherein the solid end surface is one of at least partially scored and partially perforated to facilitate piercing by the at least one of the pointed end and the sharpened edge of the medical instrument.

10. A system comprising:
    a sheath defining therein a lumen and configured to be extendable toward a tissue surface;
    an elongated medical instrument configured to be delivered through the lumen in the sheath, the elongated medical instrument having at least one of a pointed end and a sharpened edge;
    an insertion control system configured to convey the sheath to a desired location within a body, the insertion control system including a lumen terminating at a head comprising an ultrasound transducer, the lumen configured to deliver the sheath towards the tissue surface along an extension axis;
    an instrument control system configured to direct operation of the elongated medical instrument when the elongated medical instrument reaches a desired position; and
    a closed sheath tip positioned at a distal end of the sheath, the closed sheath tip having a solid end surface configured to be pierceable by the at least one of the pointed end and the sharpened edge of the elongated medical instrument, wherein when the closed sheath tip is presented at the tissue surface, the solid end surface of the closed sheath tip is configured to distribute force of impact with the tissue surface across the solid end surface and to permit the instrument to pierce the solid end surface and extend therethrough toward the tissue surface.

11. The system of claim 10, wherein the closed sheath tip is formed integrally as part of the sheath at the distal end of the sheath.

12. The system of claim 10, wherein the closed sheath tip is formed by one of attaching the solid end surface to the distal end of the sheath and attaching the solid end surface within the distal end of the sheath.

13. The system claim 12, wherein the closed sheath tip includes a coupling configured to facilitate attachment with the sheath by engaging at least one side of the sheath adjacent the distal end of the sheath.

14. The system claim 12, wherein the closed sheath tip is configured to be adhesively attached to the distal end of the sheath.

15. The system claim 12, wherein the closed sheath tip is configured to be heat-welded to the distal end of the sheath.

16. The system of claim 10, wherein the solid end surface includes a membrane configured to be pierceable by the at least one of the pointed end and the sharpened edge of the instrument.

17. The system of claim 10, wherein the solid end surface includes a flexible section configured to be pierceable by the at least one of the pointed end and the sharpened edge of the instrument and to at least one of compress and deform upon impact with the tissue surface.

18. The system of claim 10, wherein the solid end surface is one of at least partially scored and partially perforated to facilitate piercing by the at least one of the pointed end and the sharpened edge of the instrument.

19. A method comprising:
   preparing an instrument for being conveyed into a body through a lumen in a sheath, wherein the sheath is to be extended toward a tissue, the sheath including a closed sheath tip with a solid end surface at a distal end of the sheath, wherein the solid end surface is configured to be pierceable by a medical instrument having at least one of a pointed end and a sharpened edge, and wherein, when the closed sheath tip is presented at a tissue surface, the solid end surface of the closed sheath tip is configured to distribute force of impact with the tissue surface across the solid end surface and to permit the at least one of the pointed end and the sharpened edge of the instrument to pierce the solid end surface and extend therethrough toward the tissue surface;
   inserting into the body the sheath that conveys the instrument, wherein the inserting includes positioning a head of an insertion device adjacent a target location, wherein the head is disposed on a distal end of the insertion device and the head includes a ultrasound transducer disposed on the distal end;
   extending the sheath out of the head of the insertion device at an angle along an extension axis towards the tissue surface; and
   extending the instrument through the lumen to cause the at least one of a pointed end and the sharpened edge of the instrument to pierce the solid end surface of the closed sheath tip toward the tissue surface.

20. The method of claim 19, further comprising attaching the closed sheath tip to the distal end of the sheath.

* * * * *

UNITED STATES PATENT AND TRADEMARK OFFICE
CERTIFICATE OF CORRECTION

PATENT NO. : 12,296,135 B2
APPLICATION NO. : 16/205655
DATED : May 13, 2025
INVENTOR(S) : Anthony H. Siuda Page 1 of 1

It is certified that error appears in the above-identified patent and that said Letters Patent is hereby corrected as shown below:

In the Claims

In Column 11, Line 3, in Claim 13, after "system", insert --of--

In Column 11, Line 7, in Claim 14, after "system", insert --of--

In Column 11, Line 10, in Claim 15, after "system", insert --of--

Signed and Sealed this
Twelfth Day of August, 2025

Coke Morgan Stewart
*Acting Director of the United States Patent and Trademark Office*